(12) United States Patent
Fukuda et al.

(10) Patent No.: US 8,389,935 B2
(45) Date of Patent: Mar. 5, 2013

(54) CHARGED PARTICLE BEAM APPARATUS PERMITTING HIGH-RESOLUTION AND HIGH-CONTRAST OBSERVATION

(75) Inventors: Muneyuki Fukuda, Kokubunji (JP); Naomasa Suzuki, Hitachinaka (JP); Tomoyasu Shojo, Kokubunji (JP); Noritsugu Takahashi, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 441 days.

(21) Appl. No.: 12/385,612

(22) Filed: Apr. 14, 2009

(65) Prior Publication Data

US 2009/0256076 A1    Oct. 15, 2009

(30) Foreign Application Priority Data

Apr. 14, 2008  (JP) .................. 2008-104232

(51) Int. Cl.
 *G01N 23/00* (2006.01)
 *G21K 7/00* (2006.01)
(52) U.S. Cl. ........ 250/306; 250/307; 250/310; 250/311; 250/309; 250/396 ML; 250/293
(58) Field of Classification Search .................. 250/306, 250/307, 310, 311, 396 ML, 293, 309
 See application file for complete search history.

(56) References Cited

U.S. PATENT DOCUMENTS

| | | | |
|---|---|---|---|
| 5,389,787 A | 2/1995 | Todokoro et al. | |
| 6,504,164 B2 | 1/2003 | Yonezawa et al. | |
| 6,740,888 B2 | 5/2004 | Sato et al. | |

(Continued)

FOREIGN PATENT DOCUMENTS

| | | |
|---|---|---|
| JP | 05-225936 | 2/1992 |
| JP | 6-139985 | 10/1992 |

(Continued)

OTHER PUBLICATIONS

Office Action from the Japanese Patent Office, issued in corresponding Japanese Office Action No. 2008-104232, dated Nov. 27, 2012, 3 pages in Japanese, and 9 pages of its English translation.

*Primary Examiner* — Jack Berman
*Assistant Examiner* — Meenakshi Sahu
(74) *Attorney, Agent, or Firm* — Stites & Harbison, PLLC; Juan Carlos A. Marquez, Esq.; Nicholas B. Trenkle, Esq.

(57) ABSTRACT

A lower pole piece of an electromagnetic superposition type objective lens is divided into an upper magnetic path and a lower magnetic path. A voltage nearly equal to a retarding voltage is applied to the lower magnetic path. An objective lens capable of acquiring an image with a higher resolution and a higher contrast than a conventional image is provided. An electromagnetic superposition type objective lens includes a magnetic path that encloses a coil, a cylindrical or conical booster magnetic path that surrounds an electron beam, a control magnetic path that is interposed between the coil and sample, an accelerating electric field control unit that accelerates the electron beam using a booster power supply, a decelerating electric field control unit that decelerates the electron beam using a stage power supply, and a suppression unit that suppresses electric discharge of the sample using a control magnetic path power supply. Thus, whether landing energy of an electron beam varies widely, the electron beam can be focused with the electromagnetic superposition type objective lens approached to the sample.

12 Claims, 10 Drawing Sheets

U.S. PATENT DOCUMENTS

| | | |
|---|---|---|
| 2001/0011702 A1* | 8/2001 | Yonezawa et al. ............ 250/283 |
| 2003/0111616 A1* | 6/2003 | Suzuki et al. .............. 250/492.2 |
| 2008/0067396 A1 | 3/2008 | Ohshima et al. |

FOREIGN PATENT DOCUMENTS

| | | |
|---|---|---|
| JP | 06-260127 | 3/1993 |
| JP | 10-106466 | 9/1996 |
| JP | 2001-185066 | 12/1999 |
| JP | 2002-083563 A | 3/2002 |
| JP | 2003-331765 | 5/2002 |
| JP | 2007-311117 A | 11/2007 |

\* cited by examiner

CHARGED PARTICLE BEAM APPARATUS PERMITTING HIGH-RESOLUTION AND HIGH-CONTRAST OBSERVATION

CLAIM OF PRIORITY

The present application claims priority from Japanese patent application JP 2008-104232 filed on Apr. 14, 2008, the content of which is hereby incorporated by reference into this application.

BACKGROUND OF THE INVENTION

1. Field of the Invention

The present invention relates to a charged particle beam application apparatus, or more particularly, to a charged particle beam application apparatus that is used to observe, inspect, and analyze a wafer sample, which has a minute circuit pattern, with a high resolution using a low-acceleration electron beam.

2. Description of the Related Art

Various techniques have been employed in detecting a defect which occurs in fabrication of a microscopic circuit such as an LSI, measuring the length of the defect, or assessing the shape of the defect. For example, an optical inspection apparatus produces an optical image of the microscopic circuit and inspects the image to detect an abnormality. However, the resolution of the optical image is not high enough to identify a very small shape-related feature, and is not high enough to discriminate a harmful defect from a harmless defect in terms of fabrication of a circuit. A sample to be handled by such a measurement/inspection apparatus has become more and more microscopic along with advancement of technologies. For example, in a recent DRAM manufacturing process, the width of a metal wire is 90 nm or less. For a logic IC, a gate dimension has reached 45 nm.

A defect inspection technique using an electron beam provides a resolution that is high enough to image a microscopic shape-related feature of a contact hole, a gate, or a wire and a shape-related feature of a microscopic defect, and can therefore be used to classify or detect a grave defect on the basis of a contrast of a shaded image of a detective shape. Therefore, for measurement/inspection of a microscopic circuit, a measurement/inspection technique employing a charged particle beam has an advantage over the optical inspection technique.

A scanning electron microscope (SEM) that is a type of charged particle beam apparatus focuses a charged particle beam emitted from an electron source of a heating type or a field emission type so as to form a thin beam (probe-like beam), and sweeps the probe-like beam over a sample. Secondary charged particles (secondary electrons or reflected electrons) are emitted from the sample due to the sweep. Synchronously with the sweep of the primary charged particle beam, a scan image is acquired by using the secondary charged particles as a luminance signal of image data. A typical scanning electron microscope accelerates electrons emitted from the electron source using an extracting electrode interposed between the electron source, at which a negative potential is developed, and a ground at which a ground potential is developed, and irradiates the resultant electrons to the sample.

The resolution offered by a scanning charged particle microscope such as an SEM and the energy of a charged particle beam have a close relationship. When a primary charged particle beam of high energy reaches a sample (that is, when the landing energy of a primary charged particle beam is large), since primary charged particles deeply invade into the sample, an emissive range on the sample from which secondary electrons and reflected electrons are emitted expands. As a result, the emissive range becomes wider than the probe diameter of the charged particle beam, and an observational resolution is markedly degraded.

When the energy of a primary charged particle beam is excessively reduced in order to lower the landing energy, the probe diameter of the charged particle beam greatly increases due to aberrations. Eventually, the observational resolution is degraded.

Further, a contrast of an SEM image is affected by the value of a current carried by a primary charged particle beam to be irradiated to a sample. When the beam current decreases, the ratio of a secondary signal to a noise (signal-to-noise ratio) is greatly lowered and a contrast of a scan image is degraded. Preferably, the beam current value should be controlled to be as large as possible. When the energy of the primary charged particle beam is reduced, formation of a thinner probe-like beam becomes hard to do due to the Coulomb's law. When the energy of the primary charged particle beam is excessively controlled to become small, a beam current required for producing the scan image becomes insufficient. This makes it hard to acquire the scan image with a high magnification and a high resolution.

For observation with a high resolution, the energy of a primary charged particle beam, or especially, landing energy has to be appropriately controlled according to an object of observation.

As a control technology for landing energy, a retarding method is widely adopted. In the retarding method, a potential causing a primary charged particle beam to decelerate is developed at a sample in order to decrease the energy of the charged particle beam to a desired level of energy immediately before the charged particle beam reaches the sample.

For example, in JP-A-6-139985, an invention that controls the timing, at which a negative potential for retarding is developed at a sample, responsively to mounting or replacement of a sample has been disclosed.

An invention disclosed in JP-A-2001-185066 is such that: when the slope of a sample is observed according to the retarding method, the magnetic poles of an objective lens are separated into upper and lower ones, and a potential identical to the one at the sample is developed at the lower magnetic pole in efforts to minimize the adverse effect of an asymmetric retarding electric field derived from the slope of the sample (to minimize occurrence of astigmatism or reduction in efficiency in detecting secondary electrons).

In JP-A-6-260127, an invention of a potential measurement apparatus employing an electron beam has been disclosed. In the potential measurement apparatus described in JP-A-6-260127, an objective lens is divided into a yoke part for excitation and a magnetic-pole part, and is formed with two magnetic circuits. An electric field for pulling up secondary electrons is applied to the magnetic-pole part. According to JP-A-6-260127, since the objective lens is divided into two parts, the magnetic circuits can be readily designed according to the working distance between a sample and the objective lens. The diameter of the spot of an electron beam can be appropriately controlled irrespective of the working distance.

SUMMARY OF THE INVENTION

A contrast of a charged particle beam image is affected by an amount of current carried by a charged particle beam. In order to acquire a high-contrast scan image, the amount of beam current has to be increased. However, if the amount of beam current increases, a probe diameter expands due to the Coulomb's law. In order to focus a spread beam on a sample, an objective lens whose lens action is intense is needed. In the case of a magnetic-field type objective lens that narrows a beam by causing a magnetic field to leak out to the ray axis of a primary charged particle beam, a magnitude of excitation has to be increased in order to intensify the lens action.

However, as long as a magnetic field type objective lens has the conventional structure, even if a magnitude of excitation is increased, an expected lens action cannot be exerted. A magnitude of a magnetic flux occurring in a magnetic path in the objective lens is restricted by magnetic saturation. The saturated magnetic flux density in the magnetic path is determined with a magnetic material made into the magnetic path. Therefore, even if the magnitude of the magnetic flux occurring in the magnetic path increases, a magnetic flux unacceptable by the magnetic path leaks out from any part of the magnetic path. As a result, the lens action is not so intensified as the increase in the magnitude of excitation. In particular, when an accelerating voltage for a charged particle beam is increased, if a probe-like beam of high energy is produced, an incident that the beam cannot be focused may take place. Further, when a magnetic flux leaks out to the trajectory of secondary charged particles, the number of secondary charged particles reaching a detector decreases. Eventually, the quality of an acquired scan image deteriorates. When a magnitude of a magnetic flux is distributed along the axis of a beam, a lens action is exerted. Therefore, in order to approach a site of action of the lens to a sample, when a magnitude of a magnetic flux is increased, a magnetic flux distribution is developed near the desired site of action at the same time. Thus, the magnetic flux distribution has to be prevented from spreading to an axial position away from the site of action.

A resolution offered by a charged particle beam apparatus is determined with the probe diameter of a beam. When the energy of a charged particle beam decreases, the probe diameter increases due to chromatic aberration and the resolution is degraded. What is referred to as the chromatic aberration is an aberration attributable to a velocity distribution of a charged particle beam emitted from an electron source. In the retarding method, if a position at which the charged particle beam is decelerated is approached to the sample, the adverse effect of aberrations can be lessened. Therefore, when an apparatus is designed, the working distance of an objective lens is designed to be as short as possible.

However, since an objective lens and a sample into must not be physically brought into contact with each other, a technique for lessening the adverse effect of aberrations by decreasing the working distance of the objective lens has its limitations. In the case of the retarding method, since there is a large potential difference between the sample (or a sample stage) and objective lens, if the working distance is made too short, there is a risk that the sample may be destroyed with electric discharge.

The inventions described in JP-A-6-139985, JP-A-2001-185066, and JP-A-6-260127 are intended to provide an electron microscope that acquires a high-contrast and high-resolution observation image. For measurement or inspection of a microscopic circuit for which the ongoing apparatuses are designed, even when an apparatus is produced using the conventional technology described in any of JP-A-6-139985, JP-A-2001-185066, and JP-A-6-260127, basic performance such as a contrast or a resolution is insufficient. In particular, when it comes to semiconductor devices fabricated using a micro-machining technology, a signal generated from a concave part such as a contact hole or a line pattern is so feeble that observation of a microscopic object or measurement of a length is terribly hindered.

The present invention provides a charged particle beam apparatus that adopts a retarding method and a magnetic field type objective lens for a charged particle optical system. In the charged particle beam apparatus, a lower magnetic pole member of an objective lens is divided into upper and lower stages. The potential at a magnetic pole member on a sample side of the divided lower magnetic pole member is controlled into an intermediate potential between the potential at a magnetic pole member on a side far away from a sample and the potential at the sample. Thus, the charged particle beam apparatus can detect a high-contrast and high-resolution secondary-charged particle signal. Preferably, the potential at the magnetic pole member on the sample side is controlled to be equal to the potential at the sample.

Since the lower magnetic pole member is divided into the upper and lower stages, an induced magnetic flux is concentrated on the distal part of an upper magnetic pole member (upper pole piece) and the distal part of the lower magnetic pole member (lower pole piece). This is attributable to the fact that when the lower pole piece is placed adjacently to the sample, the magnetic flux extending from the upper pole piece to the lower pole piece can be concentrated on the sample. The division of the magnetic pole member makes it possible to form an objective lens that exerts a greater lens action than a conventional objective lens does. The magnetic pole member on the sample side alleviates a potential gradient between the bottom of the objective lens and the sample, and acts as means for suppressing electric discharge of the sample.

Owing to the present invention, an objective lens that exerts a satisfactory lens action on a primary charged particle beam having a large amount of beam current and requiring a high accelerating voltage can be manufactured. Eventually, a charged particle beam apparatus offering a high contrast and a high resolution can be realized. Since the charged particle beam apparatus offering a high contrast and a high resolution can be realized, a charged particle beam application apparatus permitting observation of a microscopic defect, measurement of a length, and assessment of a shape can be provided.

DESCRIPTION OF THE PREFERRED EMBODIMENTS

For brevity's sake, in relation to embodiments to be described below, examples in which the present invention is applied to an apparatus using a scanning electron microscope will be mainly described. An electromagnetic superposition type objective lens in each of the embodiments can be generally adapted to charged particle beam apparatuses including an electron beam apparatus and an ion beam apparatus. In the embodiments to be described below, apparatuses that deal with a semiconductor wafer as a sample will be described. As for samples to be dealt with by various types of charged particle beam apparatuses, in addition to the semiconductor wafer, various samples including a semiconductor substrate, a fragment of a wafer having a pattern formed therein, a chip cut out from the wafer, a hard disk, and a liquid crystal panel can be regarded as objects of inspection or measurement.

Embodiment 1

In relation to an embodiment 1, an example in which the present invention is applied to a scanning electron microscope will be described below.

Figure 1A:
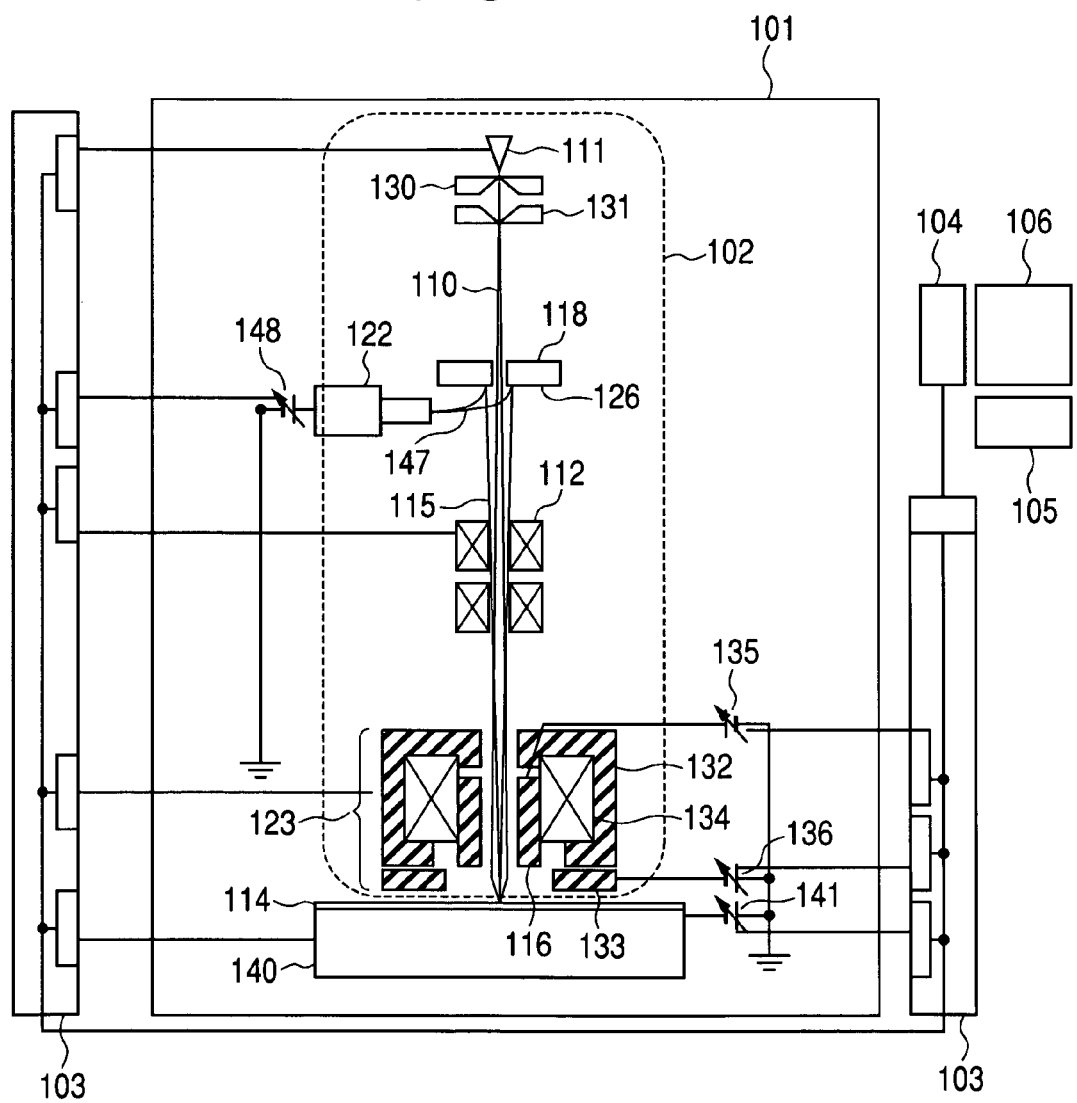
FIG. 1A is an overall constitution diagram of a charged particle beam apparatus of an embodiment 1.

FIG. 1A is an illustrative diagram showing an overall constitution of a scanning electron microscope. The scanning electron microscope of the present embodiment includes: an electron optical system 102 formed in a vacuum housing 101; an electron optical system control device 103 disposed on the perimeter of the electron optical system; a host computer 104 that controls control units included in respective control power supplies, and controls the whole of the apparatus on a centralized basis; an operator console 105 connected to the control device; and display means 106 including a monitor on which an acquired image is displayed. The electron optical system control device 103 includes a power supply unit that feeds a current or a voltage to each of the components of the electron optical system 102, and signal control lines over which control signals are transmitted to the components.

The electron optical system 102 includes: an electron source 111 that produces an electron beam (primary charged particle beam) 110; a deflector 112 that deflects the primary electron beam; an electromagnetic superposition type objective lens 123 that focuses the electron beam; a booster magnetic path member 116 that focuses or diffuses secondary particles 115 emitted from a sample 114 held on a stage; a reflecting member 118 with which the secondary particles collide; and a central detector 122 that detects collateral (tertiary) particles reemitted due to the collision. The reflecting member 118 is formed with a disk-shaped metallic member having a passage opening for a primary beam formed therein. The bottom of the reflecting member 118 realizes a secondary-particle reflecting surface 126.

An electron beam 110 emitted from the electron source 111 is accelerated due to a potential difference developed between a extracting electrode 130 and an accelerating electrode 131, and routed to the electromagnetic superposition type objective lens 123. The objective lens 123 focuses an incident primary electron beam on the sample 114.

Figure 1B:
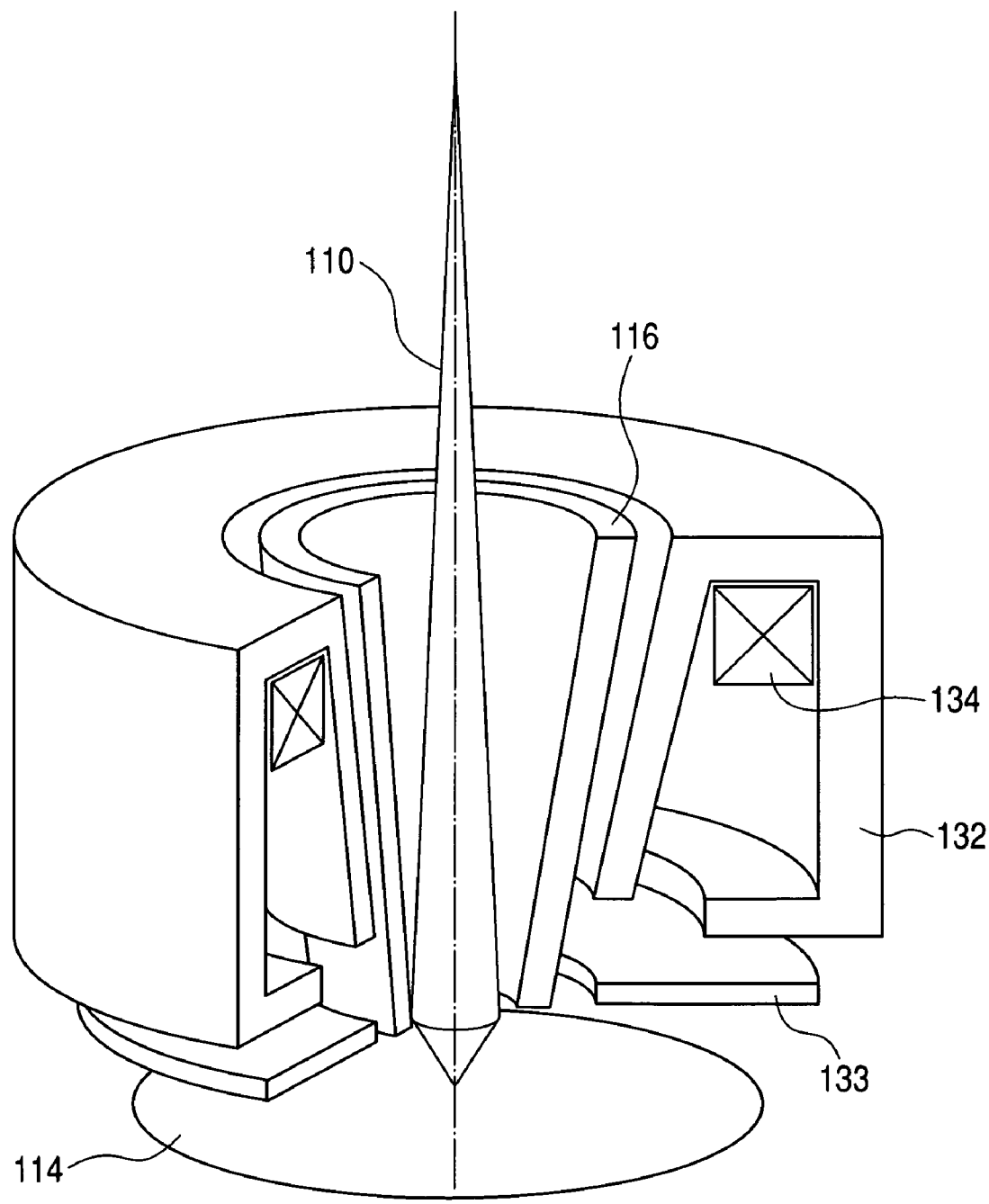
FIG. 1B is a perspective view of an objective lens included in the embodiment 1.

Referring to FIG. 1B, the internal structure of the electromagnetic superposition type objective lens 123 included in the present embodiment will be detailed below. In FIG. 1B, in addition to the internal structure of the electromagnetic superposition type objective lens 123, the sample 114 to be measured or inspected is shown.

The electromagnetic superposition type objective lens 123 in the present embodiment includes at least three members, that is, a yoke member 132 disposed around the ray axis of a primary electron beam (or the center axis of the electron optical system 102), the booster magnetic path member 116 disposed in a space between the yoke member 132 and the ray axis of the primary electron beam, and a control magnetic path member 133 disposed in a closed space defined between the bottom of the yoke member 132 and the sample 114; and a coil 134. The ray axis of the primary electron beam or the center axis of the electron optical system 102 is often aligned with the center axis of the electromagnetic superposition type objective lens 123 or vacuum housing 101.

The yoke member 132 in FIG. 1B is formed with a hollowed annular member, and the section of the yoke member 132 is shaped like a trapezoid having the side thereof, which is opposed to the ray axis of the primary electron beam, inclined. In the electromagnetic superposition type objective lens in the present embodiment, the yoke member is disposed so that the ray axis of the primary electron beam will pass through the center of the annular member. The coil 134 is sustained inside the yoke member 132 that is the annular member. A magnetic flux to be used to focus the primary electron beam is excited by the coil. A space is formed on the internal surface side of the bottom of the trapezoidal shape (the side opposed to the primary electron beam). Owing to the space, the excited magnetic flux does not form a closed magnetic path in the yoke member 132 but extends to the booster magnetic path member 116 and control magnetic path member 133. An opening through which the primary electron beam passes is formed in the top of the yoke member 132 (a falling direction of the primary electron beam) and in the bottom thereof (an emitting direction of the primary electron beam). A soft magnetic material is adopted as the material of the yoke member. Although the yoke member 132 shown in FIG. 1B is realized with the annular member having a trapezoidal section, as long as the capability to transfer the excited magnetic flux to the booster magnetic path member 116 and control magnetic path member 133 is exerted, the shape of the yoke member 132 is not limited to any specific one. For example, the section of the yoke member may be shaped like a bracket.

The booster magnetic path member 116 is a cylindrical (or conical) member formed along the internal surface (area opposed to a primary electron beam) of the annular member realizing the yoke member 132. The booster magnetic path member 116 is disposed in the electromagnetic superposition type objective lens so that the center axis of the cylinder will be aligned with the ray axis of the primary electron beam (or the center axis of the vacuum housing 101). As the material, a soft magnetic material is adopted as it is for the yoke member 132. The lower distal end of the cylinder (the distal part of the side thereof opposed to the sample) acts as a magnetic pole (pole piece) on which a magnetic flux excited by the coil is concentrated.

The control magnetic path member 133 is disposed on the side of the bottom of the yoke member 132. The control magnetic path member 133 is a disk-like or conical soft magnetic plate having an opening, through which the booster magnetic path is extended, in the center thereof. The yoke member 132 is disposed to have the axis thereof aligned with the ray axis of a primary electron beam in the electromagnetic superposition type objective lens. The opening edge of the control magnetic path member 133 realizes a magnetic pole on which a magnetic flux is concentrated. If a magnetic flux is concentrated on a gap between the magnetic pole of the control magnetic path member 133 and the magnetic pole of the booster magnetic path member 116, a lens effect that is greater than a conventional one can be exerted on a primary electron beam. A pole piece belonging to the booster magnetic path member may be called an upper magnetic pole, and a pole piece belonging to the booster magnetic path member may be called a lower magnetic pole.

Not only the control magnetic path member 133 and booster magnetic path member 116 but also the yoke member 132 and control magnetic path member 133 and the yoke member 132 and booster magnetic path member 116 are spatially separated from each other with a predetermined gap between them. However, the yoke member 132, control magnetic path member 133, and booster magnetic path member 116 are magnetically intensively coupled to one another. A magnetic flux excited by the coil 134 penetrates through the magnetic path members. The distal part of the objective lens in which the booster magnetic path member 116 and control magnetic path member 133 adjoin is formed to be so thin as to have a thickness of 3 mm or less in order to concentrate the magnetic flux adjacently to the sample. The proximal part of the objective lens in which the booster magnetic path member 116 adjoins the yoke member 132 is formed to have a thickness of 1 cm or more in order to avoid magnetic saturation.

Next, potentials to be developed at the booster magnetic path member 116, yoke member 132, and control magnetic path member 133 will be described below. The yoke member 132, control magnetic path member 133, and booster magnetic path member 116 are electrically isolated from one another with an insulating material between each pair of them. A voltage that causes the potential at the booster magnetic path member 116 relative to the potential at the yoke member 132 to be positive and that causes a potential difference from the potential at the accelerating electrode 131 to be positive is applied to the booster magnetic path member 116. The voltage is fed from a booster power supply 135. The yoke member 132 is retained at a ground potential. Therefore, the electron beam 110 passes through the booster magnetic path member 116 while being most greatly accelerated on the trajectory thereof due to the potential difference between the accelerating electrode 131 and booster magnetic path member 116.

Even in the charged particle beam apparatus of the present embodiment, the retarding method is adopted. Therefore, a decelerating electric field has to be induced between the objective lens and sample. A voltage causing the potential at the control magnetic path member 133 relative to the potential at the yoke magnetic field member 132 to be negative is applied to the control magnetic path member 133. The voltage is fed from a control magnetic path power supply 136. A voltage causing a potential difference from the potential at the booster magnetic path member 116 to be negative is applied from a stage power supply 141 to the stage 140. Therefore, the electron beam 110 having passed through the booster magnetic path member 116 is rapidly decelerated to reach the surface of the sample. Since the landing energy of a primary beam is determined solely with the potential difference between the electron source 111 and stage 140, if voltages to be applied to the electron source 111 and stage 140 respectively are controlled into predetermined values, the landing energy can be controlled into a desired value irrespective of the voltages to be applied to the booster magnetic path member 116 and accelerating electrode 131.

For a better understanding, if the relationships among the control voltage values for the foregoing components are expressed with equations, the equations are described as follows:

(1) Electron source<sample<control magnetic path member<yoke member whose potential is approximately equal to 0 V<booster magnetic path member (2) Electron source<accelerating electrode whose potential is approximately equal to 0 V<booster magnetic path member Therefore, when the voltages to be applied to the accelerating electrode 131 and booster magnetic path member 116 respectively are set to values that are positive relative to the potential at the electron source 111, the electron beam 110 can rapidly pass through the electron optical system 102. The probe diameter of the electron beam 110 on the sample can be decreased.

However, a decelerating action on the electron beam 110 exerted between the electromagnetic superposition type objective lens 123 and sample hinders a focusing action of the lens. Therefore, the electromagnetic superposition type objective lens 123 is requested to exert an intense beam focusing action. By approaching the electromagnetic superposition type objective lens 123 to the sample, the electron beam 110 can be focused more thinly. The electromagnetic superposition type objective lens 123 is therefore requested to exert the intense focusing action at a distance immediately above the sample.

Figure 2:
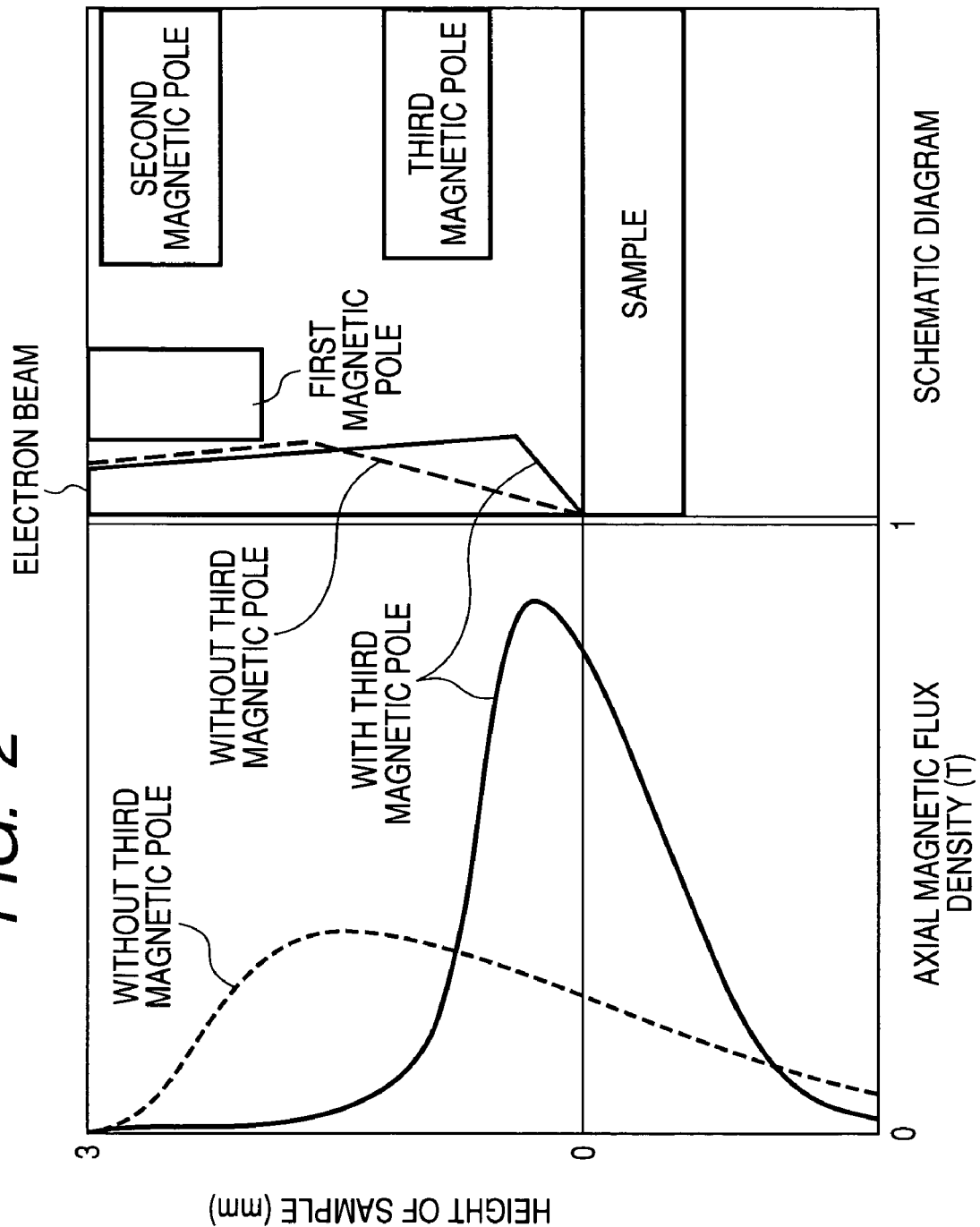
FIG. 2 shows magnetic-field distributions on the optical axes of the objective lens in the embodiment 1 and a conventional objective lens.

FIG. 2 shows axial magnetic field distributions on an objective lens with the control magnetic path member and an objective lens without it, and also shows the positional relationship among the magnetic pole members in the electromagnetic superposition type objective lens in the present embodiment. In the left part of FIG. 2, the curvature of each of curves, which are drawn with a solid line and a dashed line respectively, in the direction of the axis of abscissas expresses a magnetic flux density distribution on the axis (nearly aligned with the ray axis of a primary electron beam). The axis of ordinates indicates heights in the objective lens. The curve drawn with the solid line is concerned with the objective lens with a third magnetic pole, and the curve drawn with the dashed line is concerned with the objective lens without the third magnetic pole. Since the intensity of a lens action is nearly proportional to the degree and sharpness of the magnetic flux density distribution, the lens action of the electromagnetic superposition type objective lens can be thought to be exerted at a position associated with the peak of the curve shown in FIG. 2. In the right part of FIG. 2, a solid line depicting an electron beam schematically expresses a section of a primary electron beam that undergoes the lens action of the objective lens with the third magnetic pole, and a dashed line depicting an electron beam schematically expresses a section of a primary electron beam that undergoes the lens action of the objective lens without the third magnetic pole. In the schematic diagram of the right part of FIG. 2, the booster magnetic path member, yoke member, and control magnetic path member are shown as a first magnetic pole, a second magnetic pole, and a third magnetic pole respectively.

In the arrangement of the magnetic poles in the objective lens shown in the schematic diagram of the right part of FIG. 2, the third magnetic pole can be disposed at a position closer to a sample than a position in the related art. Therefore, the lens action exerted position of the objective lens can be more greatly approached to the sample than that can in the related art. In the case of a charged particle beam apparatus adopting the retarding method, a negative high voltage is conventionally applied to a sample in order to induce a retarding electric field, and a voltage (typically, a ground potential) higher than the voltage applied to the sample is applied to the second magnetic pole. Therefore, the distance between the second magnetic pole and sample cannot help being set to a long distance that does not bring about electrical discharge. Therefore, the conventional second magnetic pole cannot be approached to the sample as close to the sample as the third magnetic pole in the present embodiment is.

In the electromagnetic superposition type objective lens of the present embodiment, since a voltage nearly identical to a retarding voltage is applied to the third magnetic pole, the objective lens is devoid of a drawback of electric discharge between a sample and an electrode. The gap between the third magnetic pole and sample can be narrowed. Therefore, a position at which an intense lens action is exerted can be more closely approached to the sample than it is conventionally. Since a negative high voltage equivalent to the retarding voltage is applied to the control magnetic path member 133, the control magnetic path member 133 has to have a structure, which can withstand a high voltage, in relation to the yoke member 132.

The third magnetic pole is functionally equivalent to a separated magnetic path on the side of the bottom of the conventional second magnetic pole. As mentioned previously, when a magnetic path is separated, a degree of concentration of a magnetic flux on each of upper and lower magnetic poles rises. An objective lens that exerts an intense focusing action on the electron beam 110 can be realized. As a result, the electron beam 110 can be focused more thinly. Eventually, high-resolution microscopic observation is enabled.

For the foregoing reason, the electromagnetic superposition type objective lens of the present embodiment can balance a short focal length of a lens and a focusing action.

Even in the electromagnetic superposition type objective lens of the present embodiment, there is a limitation in decreasing the working distance. The limitation is determined with the upper limit of the intensity of a lens action. The intensity of a lens action becomes larger along with an increase in an amount of current to be fed to the coil 134. However, since the yoke member 132, control magnetic path member 133, and booster magnetic path member 116 are magnetically saturated, if the amount of exciting current is increased, the peak of an axial magnetic field becomes obtuse. If the peak disappears, the focusing action of the electromagnetic superposition type objective lens 123 deteriorates. High-resolution microscopic observation is disabled. The shortest distance between the electromagnetic superposition type objective lens 123 and sample making it possible to avoid the deterioration of the focusing action is the lower limit of the working distance, and shall be called the shortest focal length in the present embodiment.

Figure 3:
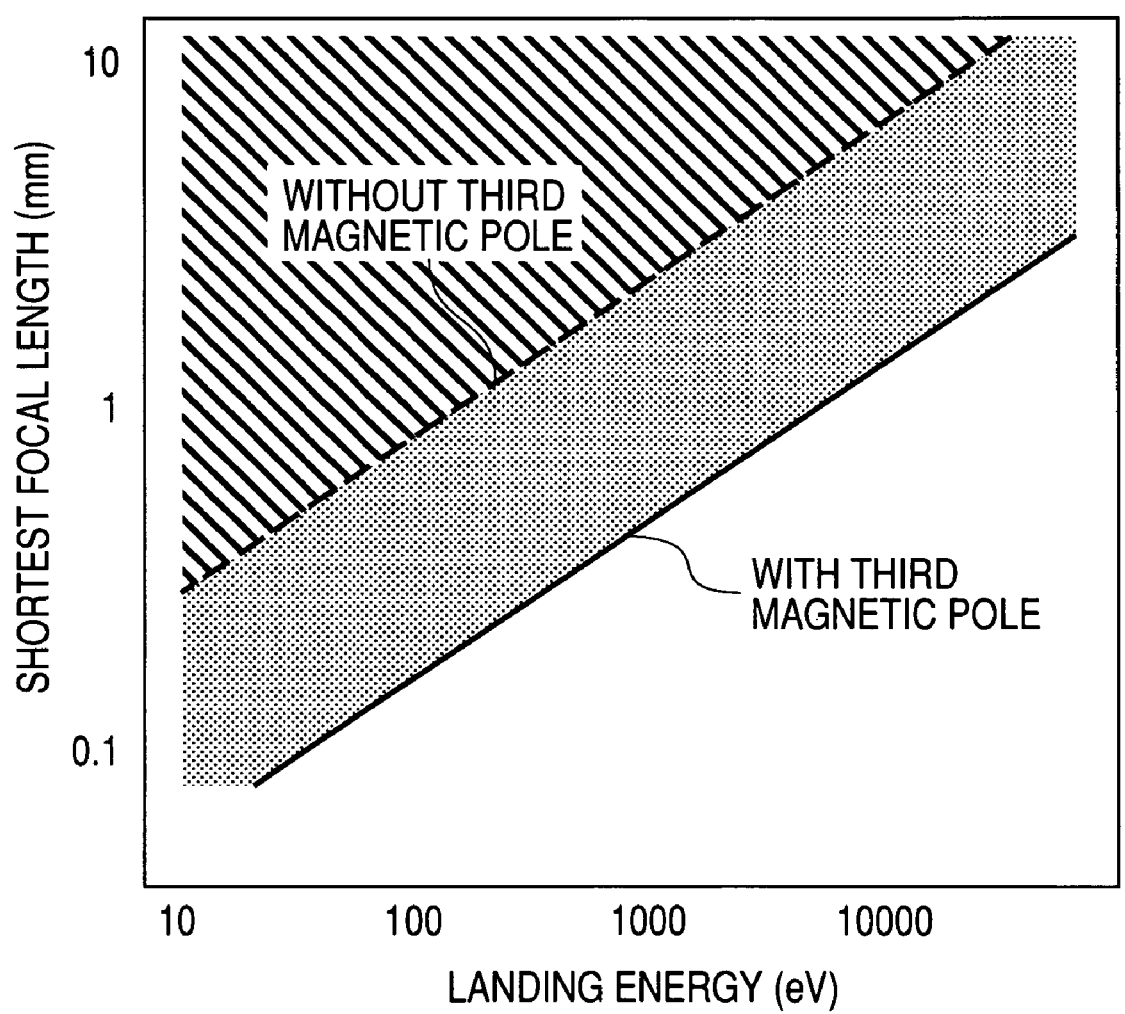
FIG. 3 shows the relationship between the shortest focal length and landing energy.

For adjustment of the electron optical system 102, an exciting current for the objective lens may have to be adjusted according to various control parameters for the optical system. For example, when the landing energy of the electron beam 110 is changed, the magnitude of excitation has to be adjusted based on a degree of adjustment to which the landing energy is adjusted. In FIG. 3, the dependency of the shortest focal length on the landing energy of an electron beam is shown by comparing the objective lens in the present embodiment with the conventional objective lens. A solid line indicates the dependency of the shortest focal length of the objective lens with a third magnetic pole, and a dashed line indicates the dependency of the shortest focal length of the objective lens without the third magnetic pole. Domains on the upper sides of the solid line and dashed line correspond to domains of in-focus points. As seen from FIG. 3, as long as the landing energy remains unchanged, the shortest focal length of the objective lens of the present embodiment including the third magnetic pole can be more greatly shortened than that of the conventional objective lens without the third magnetic pole. This is because when the focusing action on the electron beam 110 is intensified by approaching the peak of a sharp axial magnetic field to a position immediately above a sample, the magnetic saturation of the first magnetic pole can be avoided. Owing to the constitution of the electromagnetic superposition type objective lens of the present embodiment, an electron beam whose landing energy ranges from 50 eV to 10 keV can be focused by the electromagnetic superposition type objective lens having the ability to focus a beam.

The secondary particles 115 derived from irradiation of a primary beam have a negative polarity, and are therefore accelerated due to a potential difference between the sample 114 and booster magnetic path member 116. The resultant secondary particles reach the top of the electromagnetic superposition type objective lens 123. The secondary particles 115 having passed through the booster magnetic path member 116 to which a high voltage is applied are rapidly decelerated. Thereafter, the secondary particles 115 reach the upper reflective member 118 and collide with the secondary-particle collision surface 126. This results in tertiary particles 147. In a main body of the central detector 122 disposed by the side of the upper reflecting member, an attracting electric field is induced by a central fetching power supply 148. The reemitted tertiary particles are fetched into the detector with the strong electric field. Thus, a top-view image can be obtained.

An axial detector (a multi-channel plate, axial scintillator, or semiconductor detector) may be substituted for the upper reflecting member 118 and central detector 122.

A primary electron beam focused using the foregoing electromagnetic superposition type objective lens is swept over a sample. Secondary charged particles derived from the sweep are detected and imaged by the host computer 104. Thus, microscopic observation with a higher resolution than the conventional one is enabled.

Embodiment 2

In relation to the present embodiment, an example in which the present invention is applied to a review SEM will be described below.

Figure 4:
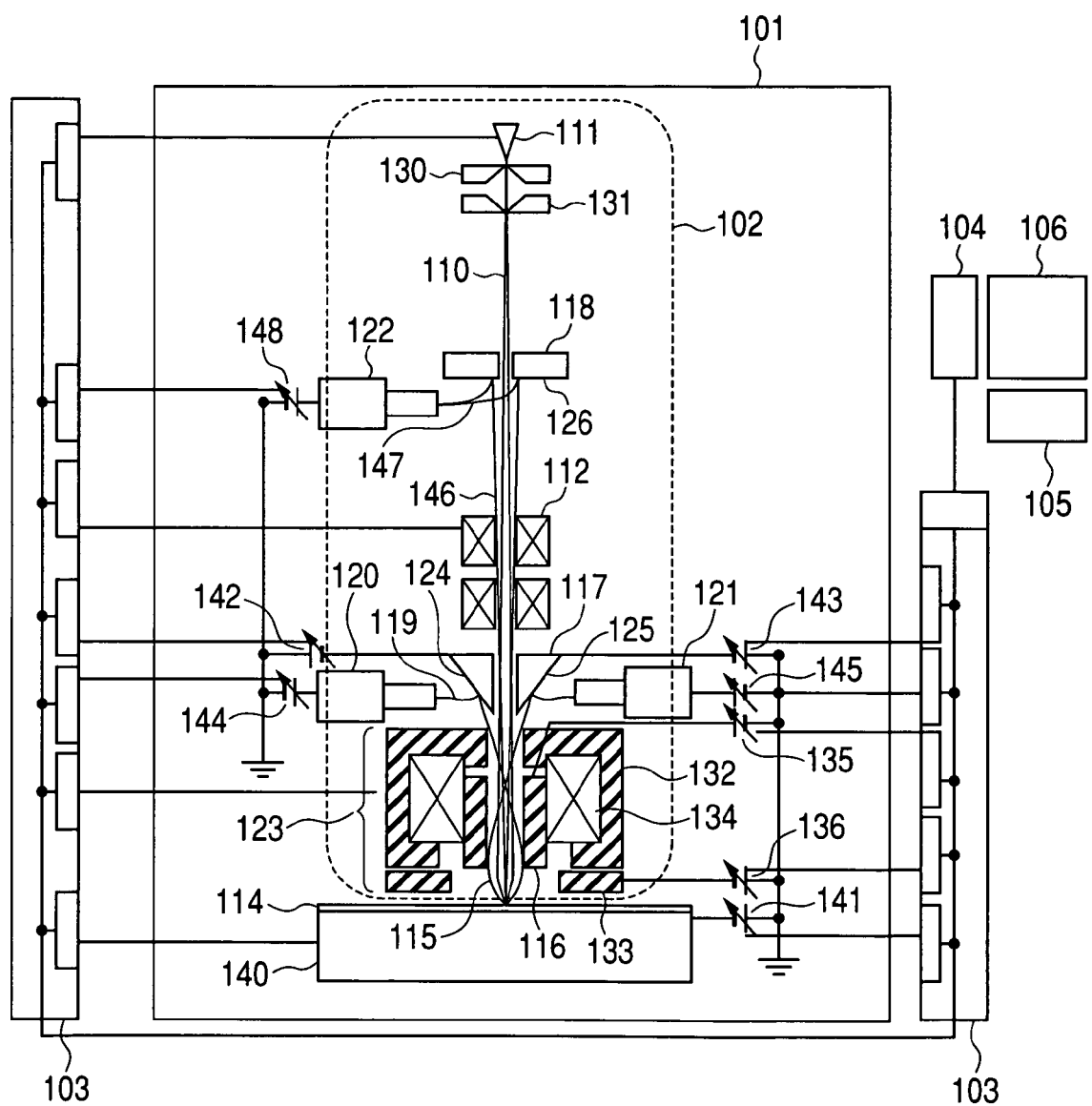
FIG. 4 is an overall constitution diagram of a charged particle beam apparatus of an embodiment 2.

FIG. 4 is an overall constitution diagram of the review SEM of the present embodiment. An iterative description of components whose operations and capabilities are identical to those of the components shown in FIG. 1 will be omitted in order to avoid a complication.

The review SEM shown in FIG. 4 broadly includes: an electron optical system 102 formed in a vacuum housing 101; an electron optical system control device 103 disposed on the perimeter of the electron optical system; a host computer 104 that controls the control units included in respective control power supplies and controls the whole of the apparatus on a centralized basis; an operator console 105 connected to the control device; and display means 106 including a monitor on which an acquired image is displayed. The electron optical system control device 103 includes a power unit that feeds a current or a voltage to each of the components of the electron optical system 102, and signal control lines over which control signals are transmitted to the respective components.

The components of the electron optical system 102 are nearly identical to those of the electron optical system described in conjunction with FIG. 1. A difference lies in that the electron optical system 102 includes a detecting capability for a shaded image. What is referred to as the shaded image is an image that has shades thereof enhanced and that is obtained by discriminating or detecting the azimuth angles and elevation angles of secondary electrons and reflected electrons that are generated from a sample to be inspected (a sample image having lights and darks associated with concave and convex parts of the surface of a sample). Using the shaded image, a defect can be efficiently detected. The electron optical system 102 of the review SEM of the present embodiment includes as discriminating means, which discriminates the azimuth angles and elevation angles of secondary particles, two reflecting members of a lower reflecting member 117 and an upper reflecting member 118, and a left detector 120, a right detector 121, and a central detector 122 that detect collateral (tertiary) particles 119 reemitted due to collision of secondary particles with the reflecting members. The lower reflecting member 117 is disposed between an electromagnetic superposition type objective lens 123 and a deflector 112. The lower reflecting member 117 is formed with a conical metal member and has a left collision surface 124 and a right collision surface 125, with which the secondary particle collide, formed on the flank thereof. The upper reflecting member 118 is formed with a disk-like metal member having a passage opening, through which a primary beam passes, formed therein. The bottom of the upper reflecting member 118 realizes a secondary-particle reflecting surface 126. The disposed positions of the left detector 120, right detector 121, and central detector 122 are not limited to those shown in FIG. 4 but may be altered. For example, if an axial detector is disposed on the secondary-particle reflecting surface of the upper reflecting member 118, the same capability as the capability of the central detector 122 can be realized. If an axial detector is disposed on each of the left collision surface 124 and right collision surface, nearly the same capabilities as those of the left detector 120 and right detector 121 can be realized. If an electromagnetic superposition type deflector (E×B deflector) is disposed on the ray axis of a primary electron beam, the primary electron beam 110 is not deflected but tertiary particles emitted from the secondary-particle reflecting surface can be guided to the central detector 122.

The secondary particles 115 derived from irradiation of a primary beam have a negative polarity and are therefore accelerated due to a potential difference between the sample 114 and booster magnetic path member 116. The secondary particles then reach the top of the electromagnetic superposition type objective lens 123. The secondary particles 115 having passed through the booster magnetic path member 116 to which a high voltage is applied are rapidly decelerated. High-velocity components (reflected electrons) contained in the secondary particles have the trajectory thereof separated from the trajectory of low-velocity components, and collide with the left collision surface 124 and right collision surface 125 of the lower reflecting member 117. Using the electromagnetic superposition type objective lens of the present embodiment, the trajectory separation can be realized and both a contrast and a resolution of a shaped image can be improved. A voltage for electric-field formation to be used to guide the tertiary particles 119, which are derived from collision of the high-velocity components of the secondary particles 115, into the left detector 120 and right detector 121 is fed from a left power supply 142 or right power supply 143 to the left collision surface 124 or right collision surface 125. At this time, the number of reflected electrons to be fetched into each of the left detector 120 and right detector 121 can be controlled. The left power supply 142 and right power supply 143 may be integrated into one unit in order to bring the left collision surface 124 and right collision surface 125 to the same potential. However, this makes it impossible to control the number of reflected electrons. Further, a voltage for electric-field formation to be used to fetch the guided reflected electrons into the detector is fed from a left fetching power supply 144 or a right fetching power supply 145 to the left detector 120 or right detector 121.

Reflected electrons advance from the sample 114 toward the lower reflecting member 117 while being rotated by a magnetic field induced by the electromagnetic superposition type objective lens 123. In consideration of the rotation caused by the magnetic field, coordinates representing each of positions on the lower reflecting member 117 with which the reflected electrons collide are associated with azimuth angles at which the respective reflected electrons are emitted from the sample. Therefore, when the left collision surface 124 and right collision surface 125 are disposed in consideration of a magnitude of rotation caused by the magnetic field, the coordinates may be associated with each of concave and convex parts of the surface of the sample.

The secondary particles 146 having the reflected electrons (strictly speaking, the high-velocity components of secondary particles) separated therefrom reach the upper reflecting member 118 located on the side of the electron source 111 at a shorter distance than the distance in which it is located away from the lower reflecting member 117. The secondary particles collide with the secondary-particle collision surface 126, whereby tertiary particles 147 are generated. In the main body of the central detector 122 disposed by the side of the upper reflecting member, an attracting electric field is induced by the central fetching power supply 148. The reemitted tertiary particles are fetched into the detector with the strong electric field. Thus, a top-view image can be acquired concurrently with an irregularities image of the surface of a sample.

The electron optical system of the review SEM of the present embodiment includes an assistant electrode for secondary-electron focusing on the side of the electron source 111 away from the electromagnetic superposition type objective lens 123. The assistant electrode is formed with a conductor plate having an opening through which the electron beam 110 passes. The magnitudes of a retarding voltage and an accelerating voltage are controlled so that a majority of secondary electrons emitted from a sample will pass through the opening. Since diffusion of the secondary electrons is suppressed by the assistant electrode, a high-contrast sample image having different lights and darks associated with the concave and convex parts of the surface of the sample can be acquired.

However, when a resist film or an insulating film is inspected in the process of forming an LSI, electrification or damage occurs due to irradiation of a charged particle beam for image formation. Due to the electrification, the trajectory of secondary electrons may change and luminous flecks (shading) may appear in an observation image. In the constitution of the apparatus of the present embodiment, a secondary-particle detector is located at a position, at which the detector is axially symmetrical to the ray axis of a primary electron beam, in order to discriminate azimuth angles of secondary particles. If a sample is electrified, the ray axis of the trajectory of the secondary particles is shifted relatively from the center axis of the detector. Shading occurs on such an occasion. If a shaded image is enhanced in order to improve the sensitivity in detecting a defect, an adverse effect of the shift of the trajectory of secondary electrons on the observation image is intensified. The shading is likely to occur readily. At this time, when only higher-velocity components are separated from the secondary particles through focusing control by the assistant electrode so that the higher-velocity components will collide with the left collision surface 124 and right collision surface 125, the shading can be suppressed. In other words, when high-resolution and high-contrast SEM observation is implemented in a state devoid of the shading and damage, an inspection method that is superior in detection sensitivity and a detection speed can be provided. In addition to beam landing, an amount of beam current carried by the primary electron beam has to be appropriately determined in line with an object of observation.

The scanning electron microscope of the present embodiment can implement automatic control in two operating modes, that is, an operating mode (review mode) in which a defect image is rapidly acquired and an operating mode (length measurement mode) in which the length of a fabricated pattern is measured or the fabricated pattern is inspected.

Two selection buttons Review Mode and Length Measurement Mode and a button Electrification Cancel are always displayed on the display screen of the display means 106. A user of the apparatus can select any of the buttons using the operator console 105. Further, an image processing unit is incorporated in the host computer 104. If a surface potentiometer is included, a degree-of-electrification distribution on a wafer can be measured and a degree-of-electrification distribution function can be stored in the host computer 104. If a Z sensor is included, the distance between the sample 114 such as the wafer and the electromagnetic superposition type objective lens 123 can be measured all the time. Pieces of information on parameters that should be specified in the electron optical system control device, a stage control device, and the image processing unit in association with the operating modes are stored in the host computer 104. If necessary, the information is transmitted to the electron optical system control device 103.

When shading occurs, if the operation of the apparatus is switched to the electrification cancel mode, the shading can be removed. When the user of the apparatus depresses the Electrification Cancel button, voltages to be applied to the assistant electrode interposed between the yoke member 132 and lower reflecting member 117 and to the lower reflecting member 117 are changed. Thus, the conditions for secondary-particle detection dependent on the electrified state of a sample are satisfied. Eventually, an image having shading removed therefrom can be produced.

The foregoing constitution is the minimum constitution of the review SEM for implementing the present embodiment. For example, a condenser lens that helps focus an electron beam or a Faraday cup that measures a beam current may be included in order to accomplish the capabilities of the present embodiment. For example, when the condenser lens is interposed between the accelerating electrode 131 and upper reflecting member 118, the condenser lens can help focus the electron beam. Further, when a current limiting diaphragm is interposed between two stages of condenser lenses, the beam current and the spread of a beam in the objective lens can be mutually independently controlled. Thus, the condenser lenses can help focus the electron beam. The deflector 112 generally falls into an electrostatic type and an electromagnetic type.

In the review mode, a defect image is acquired according to a procedure described below.

(1) A desired wafer is loaded into the apparatus.
(2) The wafer is aligned.
(3) The electron optical system is moved to a defective point represented by coordinates and an in-focus point is located.
(4) A defect observation image is acquired.

For acquiring the defect observation images of multiple points on the wafer, the steps (3) and (4) are repeated. The procedure is effective means for collecting a large number of defect observation images quickly.

If the precision in coordinates representing a defective point is found to be insufficient at the step (3), the apparatus executes the flow from step (5) to step (8) described below so as to detect accurate coordinates representing a defective point. Eventually, a defect image is acquired.

(5) The optical magnification of the electron optical system is made lower that that in the state established at the step (3).
(6) An in-focus point is located at the same position. If necessary, an electron-beam irradiation area is finely adjusted by adjusting the position of the stage or shifting an image.
(7) A low-magnification observation image is acquired, and is subjected to image processing in order to identify the defective point.
(8) The optical magnification of the electron optical system is made higher than that designated at the step (5).
(9) A defect observation image is acquired.

For acquiring defect observation images of multiple points on the wafer, the steps (3) to (9) are repeated.

If a defective point cannot be identified merely by performing image processing at the step (7), a defect observation image is acquired according to a procedure described below.

(10) The electron optical system is moved to the position of a die adjoining a defective point which is represented by coordinates, and an in-focus point is located.
(11) A low-magnification observation image is acquired.
(12) The electron optical system is moved to the defective point represented by coordinates, and an in-focus point is located.
(13) A low-magnification observation image is acquired, and compared with the observation image acquired at the step (11) in order to identify the defective point.
(14) The optical magnification of the electron optical system is raised in order to acquire an image of the identified defective point.

For acquiring defect observation images of multiple points on the wafer, the steps (10) to (14) are repeated. When the apparatus executes the steps (10) to (14), the apparatus can collect defect observation images while flexibly coping with the precision in coordinates representing a defective point or the size of the defect.

In the length measurement mode, an observation image of a fabricated pattern is acquired according to a procedure described below.

(1) A desired wafer is loaded in the apparatus.
(2) The wafer is aligned.
(3) The electron optical system is moved to an observation point represented by coordinates, and an in-focus point is located.
(4) An observation image of a fabricated pattern is acquired.

For acquiring observation images of fabricated patterns at multiple points on the wafer, the steps (3) and (4) are repeated. The procedure is effective means for quickly collecting a large number of observation images of fabricated patterns.

If the precision in coordinates representing an observation point is found to be insufficient at the step (3), an observation image is acquired according to a procedure described below.

(5) The wafer is aligned again.

(6) The electron optical system is moved to the alignment point represented by coordinates, and an in-focus point is located.

(7) An alignment observation image is acquired, and an observation point represented by coordinates is aligned through image processing.

(8) The electron optical system is moved to the observation point represented by coordinates, and an in-focus point is located.

(9) An observation image of a fabricated pattern is acquired.

For acquiring observation images of multiple points on the wafer, the steps (6) to (9) are repeated.

For assessing the shape of a fabricated pattern, an observation image of the fabricated pattern is acquired according to a procedure described below.

(10) The electron optical system is moved to an observation point, which is represented by coordinates, in a die adjoining a position at which an image is acquired at the step (9), and an in-focus point is located.

(11) A reference observation image is acquired.

(12) The electron optical system is moved to an observation point represented by coordinates, and an in-focus point is located.

(13) An observation image is acquired and compared with the reference observation image acquired at the step (11).

If the precision in coordinates representing an observation point is found to be insufficient at the step (10) or (12), an observation image is acquired according to a procedure described below.

(14) The wafer is aligned again.

(15) The electron optical system is moved to an alignment point on the adjoining die which is represented by coordinates, and an in-focus point is located.

(16) An alignment observation image is acquired, and an observation point represented by coordinates is aligned through image processing.

(17) The electron optical system is moved to a reference observation point, which is represented by coordinates, in the adjoining die, and an in-focus point is located.

(18) A reference observation image of a fabricated pattern is acquired.

(19) The electron optical system is moved to an alignment point which is represented by coordinates, and an in-focus point is located.

(20) An alignment observation image is acquired, and an observation point represented by coordinates is aligned through image processing.

(21) The electron optical system is moved to the observation point represented by coordinates, and an in-focus point is found.

(22) An observation image of a fabricated pattern is acquired and compared with the reference observation image acquired at the step (18).

For acquiring observation images of fabricated patterns at multiple points on the wafer, the steps (15) to (22) are repeated. The procedure is means capable of collecting observation images while flexibly coping with the precision in coordinates representing an observation point or the fabricated pattern.

Next, a control method for the electromagnetic superposition type objective lens included in the review SEM of the present embodiment will be described below. In either the review mode or length measurement mode, the focal point of an electron beam has to be controlled using the electromagnetic superposition type objective lens in order to locate an in-focus point. However, the scanning electron microscope of the present embodiment cannot largely change the focal position due to such restrictions as limitations in the focal length of the electromagnetic superposition type objective lens or limitations imposed on a detector according to a change in a position on a reflecting member with which secondary particles collide.

The factors causing the focal position to largely change are two of electrification of a sample and the height of the sample. When the sample electrification causes the large change in the focal position, if a retarding voltage is finely adjusted, an in-focus point can be detected without the restrictions of the limitations in the focal position of the electromagnetic superposition type objective lens and the limitation imposed on a detector. When the sample height causes the large change in the focal position, an in-focus position can be detected according to, for example, a technique described below.

(1) An electrostatic chuck is used to reduce a warp in the surface of a wafer at the time of immobilizing the wafer on the stage.

(2) The height of the stage is controlled in line with the thickness of the sample.

(3) An exciting current for the coil included in the electromagnetic superposition type objective lens is changed.

(4) A voltage to be applied to the booster magnetic path member is changed.

Owing to the foregoing constitution, reflected electrons can be discriminated and detected, and an image having a shade contrast thereof enhanced can be acquired. Eventually, a microscopic foreign matter having shallow irregularities can be highly sensitively detected.

Embodiment 3

In relation to the present embodiment, an example of a constitution of a review SEM including an electrostatic adsorption device will be described below.

Figure 5:
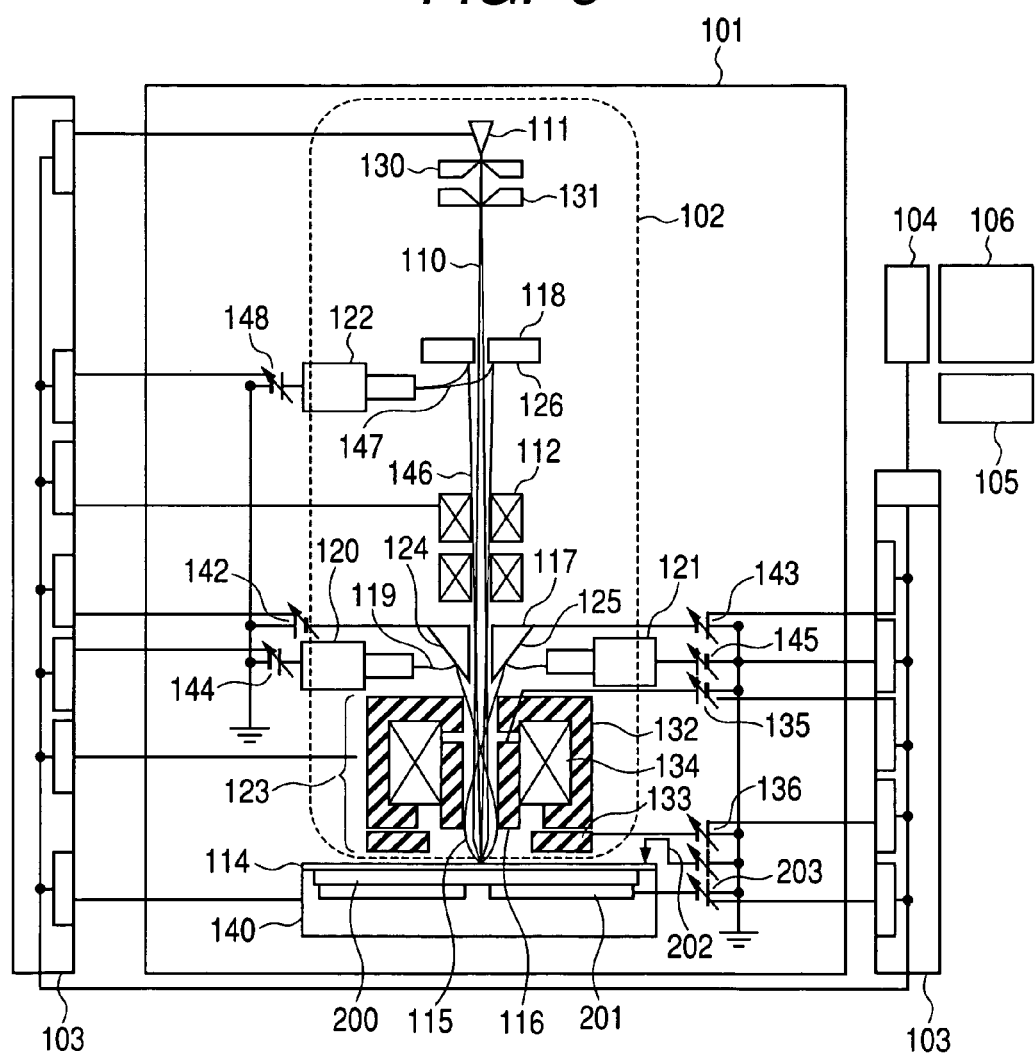
FIG. 5 is an overall constitution diagram of a charged particle beam apparatus of an embodiment 3.

FIG. 5 is an overall constitution diagram of the review SEM of the present embodiment. As for the components other than an electrostatic chuck, since the operations and capabilities thereof are identical to those of the components shown in FIG. 4, an iterative description of the components other than the electrostatic chuck will be omitted.

The review SEM of the present embodiment has a sample stage thereof provided with an electrostatic chuck mechanism. In addition to signal control lines and a power unit for the electron optical system 102, a stage control device is incorporated in the electron optical system control device 103. The stage control device includes a power unit that feeds a current or a voltage to the components of the electrostatic chuck, and signal control lines over which control signals are transmitted to the respective components.

The electrostatic chuck mechanism includes a dielectric layer 200 and an internal electrode 201, which are incorporated in the stage 140, and an internal electrode power supply 203 that applies a voltage across the internal electrode 201 and wafer 114. Along with application of a voltage, electrostatic adsorption force is generated between the internal electrode 201 and wafer 114, and the wafer 114 is adsorbed by the generated force. Depending on an adsorption method, the electrostatic chuck generally falls into a Coulomb force type and a Johnson-Rabeck force type. The Coulomb force type can reduce a current flowing across the internal electrode 201 and wafer, and the Johnson-Rabeck force type can reduce a potential difference between the internal electrode 201 and wafer. In general, the electrostatic chuck falls into a monopolar method and a bipolar method according to the internal electrode 201 located below the dielectric layer 200. The bipolar method can keep charges, which are accumulated on the dielectric layer 200 and wafer 114, neutral.

The stage 140 is provided with a contact electrode 202 to be used to bring the stage into contact with a wafer. A potential causing a potential difference from the potential at the booster magnetic path to be negative is developed at the contact electrode 202. When the potential difference between the control magnetic path member 133 and contact electrode 202 falls within ±100 V, the potential difference between the wafer and control magnetic path can be controlled. Owing to the control of the potential difference, the efficiency in focusing a primary beam or collecting and discriminating secondary particles can be controlled. Eventually, a high-resolution top-view image and a high-resolution shaded image can be obtained.

When an object of observation is a large flat-plate sample such as a wafer, if the electrostatic chuck is adopted as the sample stage, a warp of the sample is suppressed, and an observation area including an electron-beam irradiation area is flattened. Since a variance in the gap between the wafer and control magnetic path is suppressed, the magnetic poles in the objective lens can be approached to the sample accordingly. The electromagnetic superposition type objective lens of the present invention capable of balancing a short focal length of a lens and a focusing action thereof is highly compatible with the electrostatic chuck. When the electromagnetic superposition type objective lens and electrostatic chuck are used in combination, an irradiation optical system whose working distance is shorter than that of the charged particle optical system described in relation to the embodiments 1 and 2 can be realized. Thus, a primary beam can be more thinly focused, the beam diameter can be reduced, and the efficiency in collecting and discriminating secondary particles can be improved. Eventually, a high-resolution top-view image and a high-resolution shaded image can be obtained.

Figure 6A:
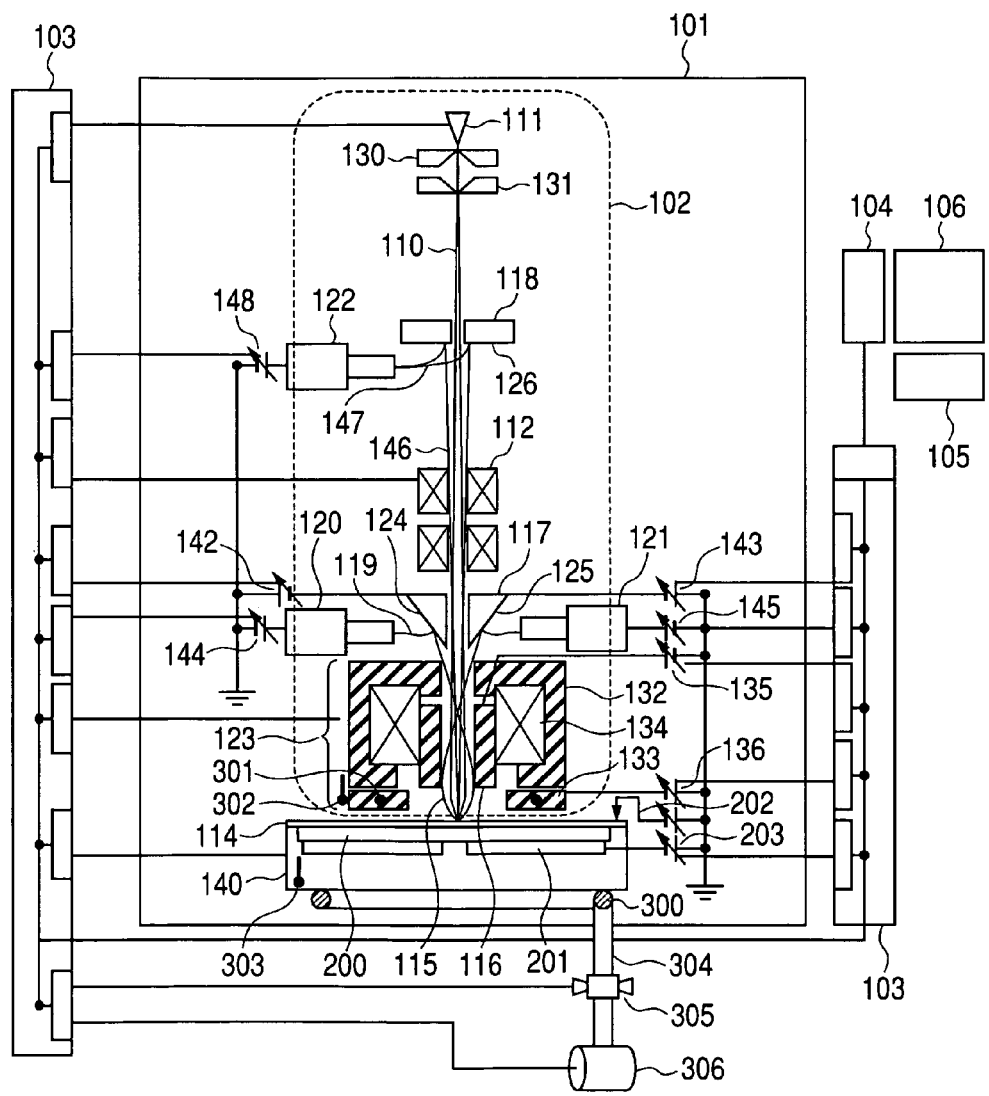
FIG. 6A is an overall constitution diagram of a charged particle beam apparatus of a variant of the embodiment 3.
Figure 6B:
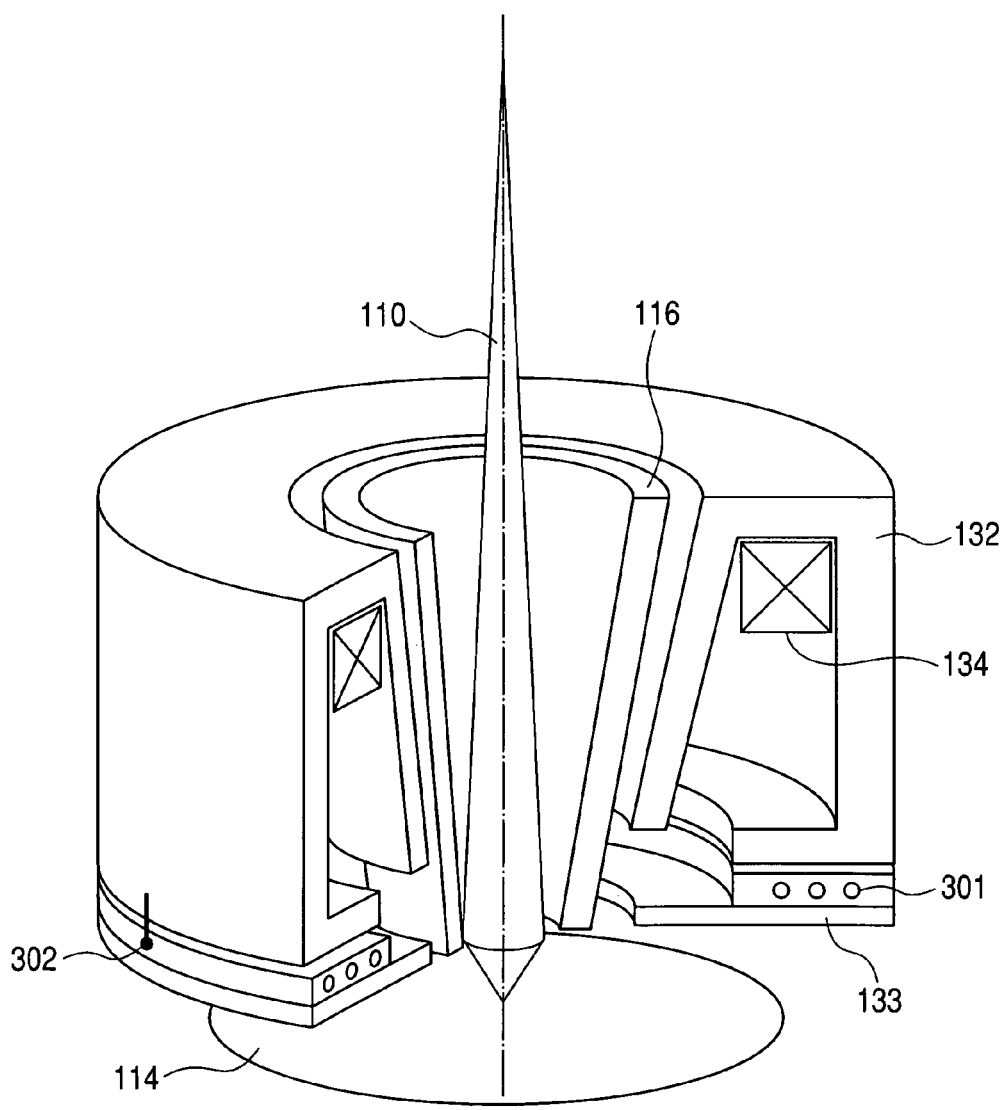
FIG. 6B is a perspective view of an objective lens included in the variant of the embodiment 3.

FIG. 6A and FIG. 6B show a variant of the review SEM including the electrostatic adsorption device. FIG. 6A is an overall constitution diagram of the review SEM, and FIG. 6B is an illustrative diagram showing the structure of an electromagnetic superposition type objective lens including a temperature control mechanism for a control magnetic path member. The electrostatic chuck dissipates heat when adsorbing the wafer 114. In particular, the Johnson-Rabeck force type electrostatic chuck dissipates much heat. Therefore, after the wafer is adsorbed by the electrostatic chuck, the wafer 114 is thermally expanded until the temperature is stabilized. When the wafer is thermally expanded, the drift of a beam landing position occurs, and a blur appears in an observation image. In addition, the alignment of the wafer is broken. The electron optical system cannot be moved to a desired point on the wafer represented by coordinates, and automatic control in the review mode or length measurement mode cannot be implemented. In order to suppress the drift, it is necessary to manage the temperature of the wafer.

In general, the electrostatic chuck mechanism includes a temperature control mechanism. The temperature of the stage 140 can be controlled by pouring an air or liquid into a pipe 300 in the electrostatic chuck. However, measurement of the temperatures of the wafer 114 and electrostatic chuck has revealed that a temperature difference is observed between the wafer and electrostatic chuck. This is attributable to the inflow of radiant heat into the wafer. The electromagnetic superposition type objective lens 123 acts as a heating source because the electromagnetic superposition type objective lens causes a large current to flow into the coil 134 due to the necessity of exciting a strong magnetic field. In particular, since the control magnetic path in the electromagnetic superposition type objective lens is opposed to the wafer with a narrow gap between them, the control magnetic path is largely involved with the inflow of radiant heat to the wafer. Therefore, a mechanism for controlling the temperature of the control magnetic path member is included in the control magnetic path member.

A cooling pipe 301 through which a coolant flows is embedded in the control magnetic path member 133. In the present embodiment, water is adopted as the coolant. When the control magnetic path member is cooled, the control magnetic path member has the capability to shield the radiation of heat dissipated from the electromagnetic superposition type objective lens to the wafer. Thus, the temperature difference between the wafer and electrostatic chuck can be suppressed. As a result, the drift of a beam landing position and misalignment of the wafer can be suppressed.

In the review SEM of the present embodiment, the control magnetic path member 133 and stage 104 are provided with thermometers 302 and 303 respectively. Temperature information measured by the thermometer 302 is transmitted to the host computer 104 over a signal transmission line that is not shown. A coolant feeding pipe 304 and a pump 306 serving as coolant circulation means are connected to the cooling pipe 300 for the electrostatic chuck. A mass-flow controller 305 is disposed as flow rate adjustment means on the path of the coolant feeding pipe 304. When receiving the temperature information measured by the thermometer 302 or 303, the host computer 104 controls the mass-flow controller 305 so as to appropriately control the flow rate of the coolant flowing through the cooling pipes 300 and 301. Thus, the temperatures of the control magnetic path member 133 and stage 104 are controlled. By including the above mechanism, the temperatures of the control magnetic member 133 and stage 104 can be highly precisely controlled, and the thermal expansion of the wafer can be managed. The precision in alignment of the wafer is upgraded to 500 nm or less. The throughput of automatic control in the review mode or length measurement mode is markedly improved. Incidentally, as the coolant, aside from a liquid such as water, an air whose heat capacity is large, such as, helium (He) may be adopted. Nevertheless, the same advantage as the advantage of water can be provided. However, the liquid is preferred because of the high cooling effect.

Owing to the review SEM of the present embodiment, the gap between the control magnetic path member and the booster magnetic path or wafer can be set to a value smaller than the conventionally adopted value. Further, the performance of the electromagnetic superposition type objective lens is improved. Eventually, a higher-resolution top-view image and a higher-resolution shaded image can be acquired.

Embodiment 4

Figure 7A:
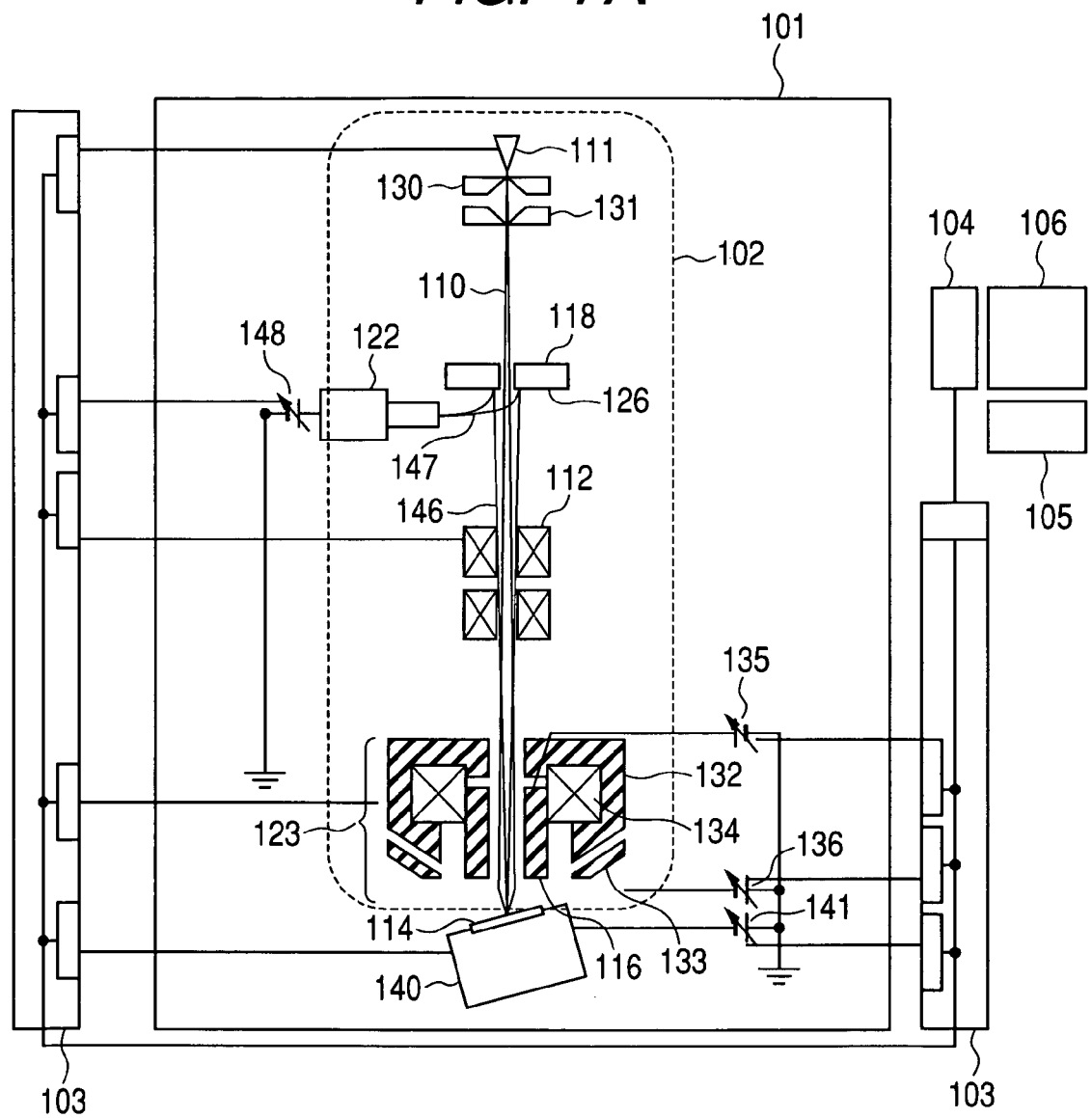
FIG. 7A is an overall constitution diagram of a charged particle beam apparatus of an embodiment 4.
Figure 7B:
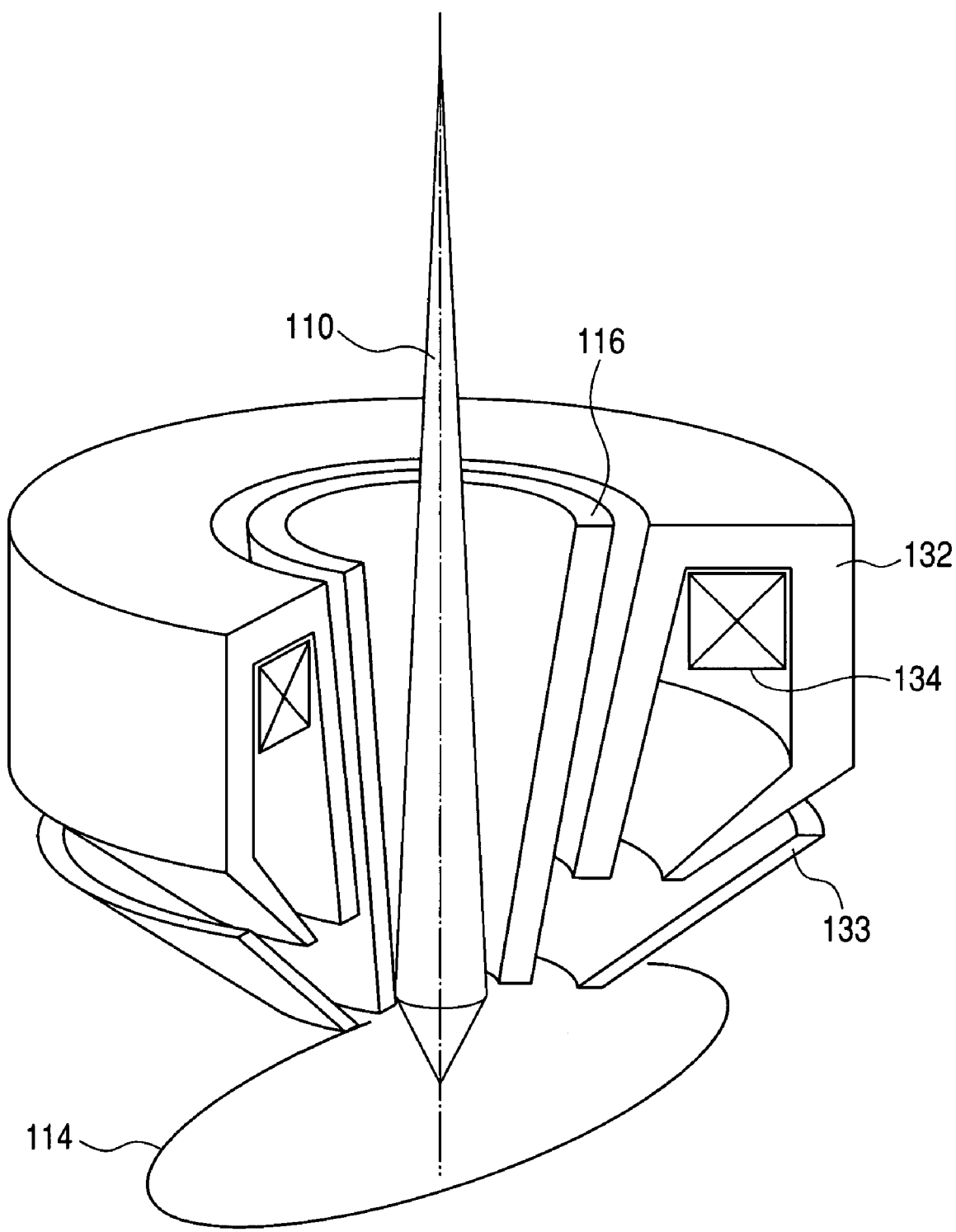
FIG. 7B is a perspective view of an objective lens included in the embodiment 4.

In relation to the present embodiment, an example in which the present invention is applied to a scanning electron microscope including a stage tilting mechanism will be described below. FIG. 7A is an overall constitution diagram of the scanning electron microscope, and FIG. 7B is an enlarged view of an electromagnetic superposition type objective lens capable of coping with stage tilting.

The scanning electron microscope of the present embodiment includes an electron optical system 102 formed in a vacuum housing 101, an electron optical system control device 103 disposed on the perimeter of the electron optical system, a host computer 104 that controls control units included in respective control power supplies and controls the whole of the apparatus on a centralized basis, an operator console 105 connected to the control device, and display means 106 including a monitor on which an acquired image is displayed. The electron optical system control device 103 includes a power supply unit that feeds a current or a voltage to each of the components of the electron optical system 102, and signal control lines over which control signals are transmitted to the respective components.

The capabilities and operations of a primary electron beam irradiation system and a secondary-particle detection system are nearly identical to the capabilities and operations described in conjunction with FIG. 1A. An iterative description will be omitted.

The scanning electron microscope of the present embodiment has a stage tilting capability. The stage 104 includes a stage tilting mechanism and a motor that drives the tilting mechanism. A tilt angle of the stage is controlled by the host computer 104 via the electron optical system control device 103. Since the scanning electron microscope has the stage tilting capability, the objective lens has a shape like the one shown in FIG. 7B. The electromagnetic superposition type objective lens shown in FIG. 7B includes, similarly to the objective lens shown in FIG. 1B, a yoke member 132, a booster magnetic path member 116, a control magnetic path member 133, and a coil 134. However, the bottom of the yoke member 132 is different from that of the yoke member shown in FIG. 1B, and is conical. This is intended to prevent the bottom of the objective lens from colliding with the sample placement surface of the stage or a sample during stage tilting. The control magnetic path member 133 is disposed along the conical surface of the bottom of the yoke member 132. The control magnetic path member 133 is supported by an insulating supporting member so that the distance between the bottom of the yoke member 132 and the control magnetic path member 133 will remain constant, though the supporting member is not shown. The slope of the conical surface of the bottom of the yoke member 132 (apex angle) is designed in line with the maximum tilt angle of the stage.

Since the electromagnetic superposition type objective lens of the present embodiment applies a voltage, which is nearly equal to the potential at a sample, to the control magnetic path member 133, the potential difference between the stage 140 and control magnetic path member 133 is smaller than the conventional one. Therefore, even when the distance from a wafer to the bottom of the objective lens varies depending on a position on the wafer, a potential distribution between the wafer and the bottom of the objective lens will not take on an abnormal shape (will not be asymmetric). Further, since the potential difference is smaller than the conventional one, electric discharge between the sample 114 and control magnetic path member 133 can be suppressed. Therefore, oblique observation of a sample with a higher resolution than a conventional one can be realized. When the booster magnetic path member 116 is shielded with the control magnetic path member 133, an electric field that efficiently attracts secondary particles can be induced in a detector disposed in a sample chamber by the side of the electron optical system 102. Eventually, a high-contrast observation image can be acquired.

In the electromagnetic superposition type objective lens of the present embodiment, the booster magnetic path member 116 has a conical shape having the sample surface side thereof sharpened. When the electromagnetic superposition type objective lens is approached to the surface of a sample with the distal part thereof thinned, a magnitude of the action of a tilted electric field in the sample chamber, which is derived from tilting of the stage, on an electron beam can be reduced, and the tendency of the spot of the probe-like electron beam toward a non-point shape can be suppressed. Further, even when the stage is tilted, the booster magnetic path member 116 sucks secondary particles so that the secondary particles will collide with the left collision surface and right collision surface of the lower reflecting member and the upper reflecting member. As a result, a high-contrast top-view image and a high-contrast shaded image can be acquired. Since the shortest distance between the stage and booster magnetic path member 116 is shortened due to tilting of the stage, a voltage to be applied to the booster magnetic path member 116 has to be approached to the potential at the control magnetic path member along with an increase in the tilt angle.

Using the scanning electron microscope of the present embodiment, a high-performance scanning electron microscope capable of balancing high-resolution and high-contrast observation performance and a stage tilting capability can be realized.

The present invention can be applied to an electron microscope or ion microscope application apparatus requested to permit high-resolution and high-contrast observation.

What is claimed is:

1. A charged particle beam apparatus that irradiates a primary charged particle beam to a sample and detects secondary charged particles generated due to the irradiation, comprising:
   an objective lens that focuses the primary charged particle beam on the sample; and
   means for applying a retarding voltage to the sample,
   wherein the objective lens includes:
   an opening through which the charged particle beam passes;
   a yoke member formed with a hollowed annular member which is disposed around a center axis of the objective lens passing through the opening;
   a booster magnetic path member disposed in a space between the yoke member and the center axis of the objective lens; and
   a control magnetic path member disposed in a space between the bottom of the yoke member and the sample; and
   a magnetic flux concentration on a gap between the booster magnetic path member and the control magnetic path member, and
   wherein the objective lens is configured to transfer the excited magnetic flux of the yoke member to the booster magnetic path member and the control magnetic path member, and
   a potential at the control magnetic path member is controlled to be a potential that is equal to or higher than the retarding voltage and that is lower than the potential at the yoke member.

2. The charged particle beam apparatus according to claim 1, wherein a potential difference between a potential at the sample and the potential at the control magnetic path member is controlled to fall within 100 V.

3. The charged particle beam apparatus according to claim 2, wherein the potential at the control magnetic path member is controlled to be equal to the potential at the sample.

4. The charged particle beam apparatus according to claim 1, wherein an accelerating voltage for use in accelerating the primary charged particle beam is applied to the booster magnetic path member.

5. The charged particle beam apparatus according to claim 1, further comprising means for electrically isolating the yoke and control magnetic path members from each other.

6. The charged particle beam apparatus according to claim 1, wherein the yoke member is brought to a ground potential.

7. The charged particle beam apparatus according to claim 1, wherein a bottom of the yoke member has a conical shape with the opening, and the control magnetic path member is realized with a magnetic plate disposed in parallel with a conical surface of the conically-shaped bottom with a predetermined gap left from the conical surface.

8. The charged particle beam apparatus according to claim 1, further comprising an electrostatic adsorption device that holds the sample.

9. The charged particle beam apparatus according to claim 7, wherein the electrostatic adsorption device includes an internal electrode that is opposed to the sample with a dielectric between them, and a contact electrode that applies the retarding voltage to the sample, further comprising:

means for retaining a potential difference between a potential at the contact electrode and the potential at the control magnetic path member at a value falling within ±100 V.

10. The charged particle beam apparatus according to claim 1, further comprising a cooling member for the control magnetic path member.

11. The charged particle beam apparatus according to claim 1, further comprising means for acquiring a shaded image of a position of irradiation of the primary charged particle beam.

12. The charged particle beam apparatus according to claim 1, wherein the control magnetic path member has two magnetic plates of an upper magnetic plate and a lower magnetic plate; and the lower magnetic plate is brought to a same potential as a potential at the sample.

* * * * *